United States Patent [19]

Kaeding

[11] 4,002,698
[45] Jan. 11, 1977

[54] METHYLATION OF TOLUENE IN THE PRESENCE OF A PHOSPHORUS-MODIFIED ACTIVATED CRYSTALLINE ALUMINOSILICATE CATALYST

[75] Inventor: Warren W. Kaeding, Westfield, N.J.

[73] Assignee: Mobil Oil Corporation, New York, N.Y.

[22] Filed: Aug. 19, 1975

[21] Appl. No.: 605,968

[52] U.S. Cl. .................... 260/671 M; 252/411 R; 252/437; 252/455 Z; 260/671 C
[51] Int. Cl.² ................. C07C 13/52; C07C 15/08
[58] Field of Search .......... 252/437, 411 R, 455 Z; 260/671 M, 671 C

[56] References Cited
UNITED STATES PATENTS

| 3,751,506 | 8/1973 | Burress | 260/671 |
|---|---|---|---|
| 3,764,563 | 10/1973 | Minachev et al. | 252/455 Z |
| 3,911,041 | 10/1975 | Kaeding et al. | 252/437 |

Primary Examiner—Delbert E. Gantz
Assistant Examiner—C. E. Spresser
Attorney, Agent, or Firm—Charles A. Huggett; Raymond W. Barclay

[57] ABSTRACT

Process for the methylation of toluene to selectively yield para-xylene by reacting toluene with a methylating agent, such as methanol, in the presence of a catalyst comprising a crystalline aluminosilicate zeolite, which zeolite has a silica/alumina ratio of at least about 12 and a constraint index, as hereinafter defined, within the approximate range of 1 to 12, the catalyst having been modified by the addition thereto of phosphorus in an amount of at least 0.5 percent by weight and activated by vapor phase treatment at a temperature between about 400° C. and about 650° C. for at least about 1 hour with a methanol/water mixture.

18 Claims, No Drawings

METHYLATION OF TOLUENE IN THE PRESENCE OF A PHOSPHORUS-MODIFIED ACTIVATED CRYSTALLINE ALUMINOSILICATE CATALYST

BACKGROUND OF THE INVENTION

1. Field of the Invention

This invention relates to a process for the methylation of toluene in the presence of a crystalline aluminosilicate catalyst modified by the addition thereto of phosphorus and activated by vapor phase treatment with a mixture of methanol and water.

2. Description of the Prior Art

Alkylation of aromatic hydrocarbons utilizing crystalline aluminosilicate catalysts has heretofore been described. U.S. Pat. No. 2,904,607 to Mattox refers to alkylation of aromatic hydrocarbons with an olefin in the presence of a crystalline metallic aluminosilicate having uniform pore openings of about 6 to 15 Angstrom units. U.S. Pat. No. 3,251,897 to Wise describes alkylation of aromatic hydrocarbons in the presence of X- or Y-type crystalline aluminosilicate zeolites, specifically such type zeolites wherein the cation is rare earth and/or hydrogen. U.S. Pat. No. 3,751,504 to Keown et al. and U.S. Pat. No. 3,751,506 to Burress describe vapor phase alkylation of aromatic hydrocarbons with olefins, e.g. benzene with ethylene, in the presence of a ZSM-5 type zeolite catalyst.

The alkylation of toluene with methanol in the presence of a cation exchanged zeolite Y has been described by Yashima et al. in the Journal of Catalysis 16, 273–280 (1970). These workers reported selective production of para-xylene over the approximate temperature range of 200° to 275° C., with the maximum yield of para-xylene in the mixture of xylenes, i.e. about 50 percent of the xylene product mixture, being observed at 225° C. Higher temperatures were reported to result in an increase in the yield of meta-xylene and a decrease in production of para- and ortho-xylenes.

While the above-noted prior art is considered of interest in connection with the subject matter of the present invention, the methylation process described herein utilizing a catalyst of a crystalline aluminosilicate zeolite having a silica/alumina ratio of at least about 12, a constraint index within the approximate range of 1 to 12 and which has been modified by the addition thereto of phosphorus in an amount of at least 0.5 percent by weight and activated by vapor phase treatment with a methanol/water mixture as described herein, has not, insofar as is known, been heretofore described.

Of the xylene isomers, i.e. ortho-, meta- and paraxylene, meta-xylene is the least desired product, with ortho-and para-xylene being the more desired products. Para-xylene is of particular value being useful in the manufacture of terephthalic acid which is an intermediate in the manufacture of synthetic fibers such as "Dacron". Mixtures of xylene isomers either along or in further admixture with ethylbenzene, generally containing a concentration of about 24 weight percent para-xylene in the equilibrium mixture, have been previously separated by expensive superfraction and multistage refrigeration steps. Such process, as will be realized, has involved high operation costs and has a limited yield.

SUMMARY OF THE INVENTION

In accordance with the present invention, there has been discovered a process for selectively producing para-xylene by reaction of toluene with a methylating agent in the presence of a catalyst comprising a crystalline aluminosilicate zeolite, said zeolite having a silica to alumina ratio of at least about 12, a constraint index within the approximate range of 1 to 12 and which has been modified by the addition thereto of phosphorus and activated by vapor phase treatment with a methanol/water mixture. The latter treatment significantly increases the catalyst activity in a permanent fashion and provides attractive yields of xylenes rich in the para isomer.

The present process comprises methylation of toluene in the presence of a particular phosphorus-modified crystalline aluminosilicate catalyst which has undergone activation as a result of treatment with a methanol/water mixture at a temperature of about 400° C. and about 650° C. for at least about 1 hour. The catalyst employed is modified by the addition thereto of phosphorus in an amount of at least about 0.5 percent by weight. The content of phosphorus may be as high as about 25 percent by weight.

DESCRIPTION OF SPECIFIC EMBODIMENTS

The zeolite catalysts herein described are members of a novel class of zeolites exhibiting some unusual properties. These catalysts induce profound transformations of aliphatic hydrocarbons to aromatic hydrocarbons in commercially desirable yields and are generally highly effective in conversion reactions involving aromatic hydrocarbons. Although they have unusually low alumina contents, i.e. high silica to alumina ratios, they are very active even when the silica to alumina ratio exceeds 30. The activity is surprising since catalytic activity is generally attributed to framework aluminum atoms and cations associated with these aluminum atoms. These catalysts retain their crystallinity for long periods in spite of the presence of steam at high temperature which induces irreversible collapse of the framework of other zeolites, e.g. of the X and A type. Furthermore, carbonaceous deposits, when formed, may be removed by burning at higher than usual temperatures to restore activity. In many environments the zeolites of this class exhibit very low coke forming capability, conducive to very long times on stream between burning regenerations.

An important characteristic of the crystal structure of this class of zeolites is that it provides constrained access to, and egress from the intracrystalline free space by virtue of having a pore dimension greater than about 5 Angstroms and pore windows of about a size such as would be provided by 10-membered rings of oxygen atoms. It is to be understood, of course, that these rings are those formed by the regular disposition of the tetrahedra making up the anionic framework of the crystalline aluminosilicate, the oxygen atoms themselves being bonded to the silicon or aluminum atoms at the centers of the tetrahedra. Briefly, the preferred type catalysts useful in this invention possess, in combination: a silica to alumina ratio of at least about 12; and a structure providing constrained access to the crystalline free space.

The silica to alumina ratio referred to may be determined by conventional analysis. This ratio is meant to represent, as closely as possible, the ratio in the rigid anionic framework of the zeolite crystal and to exclude aluminum in the binder or in cationic or other form within the channels. Although catalysts with a silica to alumina ratio of at least 12 are useful, it is preferred to use catalysts having higher ratios of at least about 30. Such catalyst, after activation, acquire an intracrystalline sorption capacity for normal hexane which is greater than that for water, i.e. they exhibit "hydrophobic" properties. It is believed that this hydrophobic character is advantageous in the present invention.

The type zeolites useful in this invention freely sorb normal hexane and have a pore dimension greater than about 5 Angstroms. In addition, the structure must provide constrained access to larger molecules. It is sometimes possible to judge from a known crystal structure whether such constrained access exists. For example, if the only pore windows in a crystal are formed by 8-membered rings of oxygen atoms, then access by molecules of larger cross-section than normal hexane is excluded and the zeolite is not of the desired type. Windows of 10-membered rings are preferred, although, in some instances, excessive puckering or pore blockage may render these catalysts ineffective. Twelve-membered rings do not generally appear to offer sufficient constraint to produce the advantageous conversions, although puckered structures exist such as TMA offretite which is a known effective zeolite. Also, structures can be conceived, due to pore blockage or other cause, they may be operative.

Rather than attempt to judge from crystal structure whether or not a catalyst possesses the necessary constrained access, a simple determination of the "constraint index" may by made by passing continuously a mixture of an equal weight of normal hexane and 3-methylpentane over a small sample, approximately 1 gram or less, of catalyst at atmospheric pressure according to the following procedure. A sample of the catalyst, in the form of pellets or extrudate, is crushed to a particle size about that of coarse sand and mounted in a glass tube. Prior to testing, the catalyst is treated with a stream of air at 1000° F. for at least 15 minutes. The catalyst is then flushed with helium and the temperature adjusted between 550° F. and 950° F. to give an overall conversion between 10% and 60%. The mixture of hydrocarbons is passed at 1 liquid hourly spaced velocity (i.e., 1 volume of liquid hydrocarbon per volume of catalyst per hour) over the catalyst with a helium dilution to give a helium to total hydrocarbon mole ratio of 4:1. After 20 minutes on stream, a sample of the effluent is taken and analyzed, most conveniently by gas chromatography, to determine the fraction remaining unchanged for each of the two hydrocarbons.

The "constraint index" is calculated as follows:

$$\text{Constraint Index} = \frac{\log_{10} \text{(fraction of n-hexane remaining)}}{\log_{10} \text{(fraction of 3-methylpentane remaining)}}$$

The constraint index approximates the ratio of the cracking rate constants for the two hydrocarbons. Catalysts suitable for the present invention are those having a constraint index in the approximate range of 1 to 12. Constraint Index (CI) values for some typical catalysts are:

| CAS | C.I. |
|---|---|
| ZSM-5 | 8.3 |
| ZSM-11 | 8.7 |
| ZSM-12 | 2 |
| ZSM-38 | 2 |
| ZSM-35 | 4.5 |
| TMA Offretite | 3.7 |
| Beta | 0.6 |
| ZSM-4 | 0.5 |
| H-Zeolon | 0.5 |
| REY | 0.4 |
| Amorphous Silica-Alumina | 0.6 |
| Erionite | 38 |

It is to be realized that the above constraint index values typically characterize the specified zeolites but that such are the cumulative result of several variables used in determination and calculation thereof. Thus, for a given zeolite depending on the temperature employed within the aforenoted range of 550° F. to 950° F., with accompanying conversion between 10% and 60%, the constraint index may vary within the indicated approximate range of 1 to 12. Likewise, other variables such as the crystal size of the zeolite, the presence of possibly occluded contaminants and binders intimately combined with the zeolite may affect the constraint index. It will accordingly be understood by those skilled in the art that the constraint index, as utilized herein, while affording a highly useful means for characterizing the zeolites of interest is approximate, taking into consideration the manner of its determination, with the probability, in some instances, of compounding variable extremes. However, in all instances, at a temperature within the above-specified range of 550° F. to 950° F., the constraint index will have a value for any given zeolite of interest herein within the approximate range of 1 to 12.

The class of zeolites defined herein is exemplified by ZSM-5, ZSM-11, ZSM-12, ZSM-35, ZSM-38, and other similar materials. Recently issued U.S. Pat. No. 3,702,886 describing and claiming ZSM-5 is incorporated herein by reference.

ZSM-11 is more particularly described in U.S. Pat. No. 3,709,979, the entire contents of which are incorporated herein by reference.

ZSM-12 is more particularly described in U.S. Pat. No. 3,832,449, the entire contents of which are incorporated herein by reference.

ZSM-38 is more particularly described in U.S. Application Ser. No. 528,060, filed Nov. 29, 1974. This zeolite can be identified, in terms of mole ratios of oxides and in the anhydrous state, as follows:

$$(0.3-2.5)R_2O : (0-0.8)M_2O : Al_2O_3 : > 8 SiO_2$$

wherein R is an organic nitrogen-containing cation derived from a 2-(hydroxyalkyl) trialkylammonium compound and M is an alkali metal cation, and is characterized by a specified X-ray powder diffraction pattern.

In a preferred synthesized form, the zeolite has a formula, in terms of mole ratios of oxides and in the anhydrous state, as follows:

$(0.4-2.5)R_2O : (0-0.6) M_2O : Al_2O_3 : xSiO_2$ wherein R is an organic nitrogen-containing cation derived from a 2-(hydroxyalkyl)trialkylammonium compound, wherein alkyl is methyl, ethyl or a combination thereof, M is an alkali metal, especially sodium, and x is from greater than 8 to about 50.

The synthetic ZSM-38 zeolite possesses a definite distinguishing crystalline structure whose X-ray diffraction pattern shows substantially the significant lines set forth in Table I. It is observed that this X-ray diffraction pattern (significant lines) is similar to that of natural ferrierite with a notable exception being that natural ferrierite patterns exhibit a significant line at 11.33A.

TABLE I

| d(A) | I/Io |
|---|---|
| 9.8 ± 0.20 | Strong |
| 9.1 ± 0.19 | Medium |
| 8.0 ± 0.16 | Weak |
| 7.1 ± 0.14 | Medium |
| 6.7 ± 0.14 | Medium |
| 6.0 ± 0.12 | Weak |
| 4.37 ± 0.09 | Weak |
| 4.23 ± 0.09 | Weak |
| 4.01 ± 0.08 | Very Strong |
| 3.81 ± 0.08 | Very Strong |
| 3.69 ± 0.07 | Medium |
| 3.57 ± 0.07 | Very Strong |
| 3.51 ± 0.07 | Very Strong |
| 3.34 ± 0.07 | Medium |
| 3.17 ± 0.06 | Strong |
| 3.08 ± 0.06 | Medium |
| 3.00 ± 0.06 | Weak |
| 2.92 ± 0.06 | Medium |
| 2.73 ± 0.06 | Weak |
| 2.66 ± 0.05 | Weak |
| 2.60 ± 0.05 | Weak |
| 2.49 ± 0.05 | Weak |

A further characteristic of ZSM-38 is its sorptive capacity providing said zeolite to have increased capacity for 2-methylpentane (with respect to n-hexane sorption by the ratio n-hexane/2-methyl-pentane) when compared with a hydrogen form of natural ferrierite resulting from calcination of an ammonium exchanged form. The characteristic sorption ratio n-hexane/2-methylpentane for ZSM-38 (after calcination at 600° C.) is less than 10, whereas that ratio for the natural ferrierite is substantially greater than 10, for example, as high as 34 or higher.

Zeolite ZSM-38 can be suitably prepared by preparing a solution containing sources of an alkali metal oxide, preferably sodium oxide, an organic nitrogen-containing oxide, an oxide of aluminum, an oxide of silicon and water and having a composition, in terms of mole ratios of oxides, falling within the following ranges:

| R+ | Broad | Preferred |
|---|---|---|
| R+ + M+ | 0.12-1.0 | 0.3-0.9 |
| OH⁻/SiO₂ | 0.05-0.5 | 0.07-0.49 |
| H₂O/OH⁻ | 41-500 | 100-250 |
| SiO₂/Al₂O₃ | 8.8-200 | 12-60 | wherein R is an organic nitrogen-containing cation derived from a 2-(hydroxyalkyl) trialkylammonium compound and M is an alkali metal ion, and maintaining the mixture until crystals of the zeolite are formed. (The quantity of OH⁻ is calculated only from the inorganic sources of alkali without any organic base contribution). Thereafter, the crystals are separated from the liquid and recovered. Typical reaction conditions consist of heating the foregoing reaction mixture to a temperature of from about 90° C. to about 400° C. for a period of time of from about 6 hours to about 100 days. A more preferred temperature range is from about 150° C. to about 400° C. with the amount of time at a temperature in such range being from about 6 hours to about 80 days.

The digestion of the gel particles is carried out until crystals form. The solid product is separated from the reaction medium, as by cooling the whole to room temperature, filtering and water washing. The crystalline product is thereafter dried, e.g. at 230° F. for from about 8 to 24 hours.

ZSM-35 is more particularly described in U.S. Application Ser. No. 528,061, filed November 29, 1974. This zeolite can be identified, in terms of mole ratios of oxides and in the anhydrous state, as follows:

$(0.3-2.5)R_2O : (0-0.8)M_2O : Al_2O_3 : 8 SiO_2$ wherein R is an organic nitrogen-containing cation derived from ethylenediamine or pyrrolidine and M is an alkali metal cation, and is characterized by a specified X-ray powder diffraction pattern.

In a preferred synthesized form, the zeolite has a formula, in terms of mole ratios of oxides and in the anhydrous state, as follows:

$(0.4-2.5)R_2O : (0.0.6) M_2O : Al_2O_3 : xSiO_2$ wherein R is an organic nitrogen-containing cation derived from ethylenediamine or pyrrolidine, M is an alkali metal, especially sodium, and x is from greater than 8 to about 50.

The synthetic ZSM-35 zeolite possesses a definite distinguishing crystalline structure whose X-ray diffraction pattern shows substantially the significant lines set forth in Table II. It is observed that this X-ray diffraction pattern (with respect to significant lines) is similar to that of natural ferrierite with a notable exception being that natural ferrierite patterns exhibit a significant line at 11.33A. Close examination of some individual samples of ZSM-35 may show a very weak line at 11.3–11.5A. This very weak line, however, is determined not to be a significant line for ZSM-35.

TABLE II

| d(A) | I/I₀ |
|---|---|
| 9.6 ± 0.20 | Very Strong - Very Very Strong |
| 7.10 ± 0.15 | Medium |
| 6.98 ± 0.14 | Medium |
| 6.64 ± 0.14 | Medium |
| 5.78 ± 0.12 | Weak |
| 5.68 ± 0.12 | Weak |
| 4.97 ± 0.10 | Weak |
| 4.58 ± 0.09 | Weak |
| 3.99 ± 0.08 | Strong |
| 3.94 ± 0.08 | Medium Strong |
| 3.85 ± 0.08 | Medium |
| 3.78 ± 0.08 | Strong |
| 3.74 ± 0.08 | Weak |
| 3.66 ± 0.07 | Medium |
| 3.54 ± 0.07 | Very Strong |
| 3.48 ± 0.07 | Very Strong |
| 3.39 ± 0.07 | Weak |
| 3.32 ± 0.07 | Weak Medium |
| 3.14 ± 0.06 | Weak Medium |
| 2.90 ± 0.06 | Weak |
| 2.85 ± 0.06 | Weak |
| 2.71 ± 0.05 | Weak |
| 2.65 ± 0.05 | Weak |
| 2.62 ± 0.05 | Weak |
| 2.58 ± 0.05 | Weak |
| 2.54 ± 0.05 | Weak |
| 2.48 ± 0.05 | Weak |

A further characteristic of ZSM-35 is its sorptive capacity proving said zeolite to have increased capacity for 2-methylpentane (with respect to n-hexane sorption by the ratio n-hexane/2-methylpentane) when compared with a hydrogen form of natural ferrierite resulting from calcination of an ammonium exchanged form. The characteristic sorption ratio n-hexane/2-methylpentane for ZSM-35 (after calcination at 600° C.) is less than 10, whereas that ratio for the natural ferrierite is substantially greater than 10, for example, as high as 34 or higher.

Zeolite ZSM-35 can be suitably prepared by preparing a solution containing sources of an alkali metal oxide, preferably sodium oxide, an organic nitrogen-containing oxide, as oxide of aluminum, an oxide of silicon and water and having a composition, in terms of mole ratios of oxides, falling within the following ranges:

| R+ | Broad | Preferred |
|---|---|---|
| R+ + M+ | 0.2–1.0 | 0.3–0.9 |
| OH⁻/SiO₂ | 0.05–0.5 | 0.07–0.49 |
| H₂O/OH⁻ | 41–500 | 100–250 |
| SiO₂/Al₂O₃ | 8.8–200 | 12–60 | wherein R is an organic nitrogen-containing cation derived from pyrrolidine or ethylenediamine and M is an alkali metal ion, and maintaining the mixture until crystals of the zeolite are formed. (The quantity of OH⁻ is calculated only from the inorganic sources of alkali without any organic base contribution). Thereafter, the crystals are separated from the liquid and recovered. Typical reaction conditions consist of heating the foregoing reaction mixture to a temperature of from about 90° C. to about 400° C. for a period of time of from about 6 hours to about 100 days. A more preferred temperature range is from about 150° C. to about 400° C. with the amount of time at a temperature in such range being from about 6 hours to about 80 days.

The digestion of the gel particles is carried out until crystals form. The solid product is separated from the reaction medium, as by cooling the whole to room temperature, filtering and water washing. The crystalline product is dried, e.g. at 230° F., for from about 8 to 24 hours.

The specific zeolites described, when prepared in the presence of organic cations, are catalytically inactive, possibly because the intracrystalline free space is occupied by organic cations from the forming solution. They may be activated by heating in an inert atmosphere at 1000° F. for one hour, for example, followed by base exchange with ammonium salts followed by calcination at 1000° F. in air. The presence of organic cations in the forming solution may not be absolutely essential to the formation of this type zeolite; however, the presence of these cations does appear to favor the formation of this special type of zeolite. More generally, it is desirable to activate this type catalyst by base exchange with ammonium salts followed by calcination in air at about 1000° F. for from about 15 minutes to about 24 hours.

Natural zeolites may sometimes be converted to this type zeolite catalyst by various activation procedures and other treatments such as base exchange, steaming, alumina extraction and calcination, in combinations. Natural minerals which may be so treated include ferrierite, brewsterite, stilbite, dachiardite, epistilbite, heulandite, and clinoptilolite. The preferred crystalline aluminosilicates are ZSM-5, ZSM-11, ZSM-12, ZSM-38 and ZSM-35, with ZSM-5 particularly preferred.

The catalysts of this invention may be in the hydrogen form or they may be base exchanged or impregnated to contain ammonium or a metal cation complement. It is desirable to calcine the catalyst after base exchange. The metal cations that may be present include any of the cations of the metals of Groups I through VIII of the periodic table. However, in the case of Group IA metals, the cation content should in no case be so large as to effectively inactivate the catalyst.

In a preferred aspect of this invention, the catalysts hereof are selcted as those having a crystal framework density, in the dry hydrogen form, of not substantially below about 1.6 grams per cubic centimeter. It has been found that zeolites which satisfy all three of these criteria are most desired because they tend to maximize the production of gasoline boiling range hydrocarbon products. Therefore, the preferred catalysts of this invention are those having a constraint index as defined above of about 1 to about 12, a silica to alumina ratio of at least about 12 and a dried crystal density of not less than about 1.6 grams per cubic centimeter. The dry density for known structures may be calculated from the number of silicon plus aluminum atoms per 1000 cubic Angstroms, as given, e.g., on page 19 of the article on Zeolite Structure by W. M. Meir. This paper, the entire contents of which are incorporated herein by reference, is included in "Proceedings of the Conference on Molecular Sieves, London, April 1967", published by the Society of Chemical Industry, London, 1968. When the crystal structure is unknown, the crystal framework density may be determined by classical pyknometer techniques. For example, it may be determined by immersing the dry hydrogen form of the zeolite in an organic solvent which is not sorbed by the crystal. It is possible that the unusual sustained activity and stability of this class of zeolites is associated with its high crystal anionic framework density of not less than about 1.6 grams per cubic centimeter. This high density, of course, must be associated with a relatively small amount of free space within the crystal, which might be expected to result in more stable structures. This free space, however, is important as the locus of catalytic activity.

Crystal framework densities of some typical zeolites are:

| Zeolite | Void Volume | Framework Density |
|---|---|---|
| Ferrierite | 0.28 cc/cc | 1.76 g/cc |
| Mordenite | .28 | 1.7 |
| ZSM-5, -11 | .29 | 1.79 |
| Dachiardite | .32 | 1.72 |
| L | .32 | 1.61 |
| Clinoptilolite | .34 | 1.71 |
| Laumontite | .34 | 1.77 |
| ZSM-4 (Omega) | .38 | 1.65 |
| Heulandite | .39 | 1.69 |
| P | .41 | 1.57 |
| Offretite | .40 | 1.55 |
| Levynite | .40 | 1.54 |
| Erionite | .35 | 1.51 |
| Gmelinite | .44 | 1.46 |
| Chabazite | .47 | 1.45 |
| A | .5 | 1.3 |
| Y | .48 | 1.27 |

When synthesized in the alkali metal form, the zeolite is conveniently converted to the hydrogen form, generally by intermediate formation of the ammonium form as a result of ammonium ion exchange and calcination of the ammonium form to yield the hydrogen form. In addition to the hydrogen form, other forms of the zeolite wherein the original alkali metal has been reduced to less than about 1.5 percent by weight may be used. Thus, the original alkali metal of the zeolite may be replaced by ion exchange with other suitable ions of Groups IB to VIII of the Periodic Table including, by way of example, nickel, zinc, calcium or rare earth metals.

The crystals of zeolite in a form substantially free of alkali metal, i.e. containing less than about 1.5 weight percent alkali metal and preferably having at least a portion of the original cations associated therewith replaced by hydrogen, are then contacted with a phosphorus compound.

Representative phosphorus-containing compounds include derivatives of groups represented by $PX_3$, $RPX_2$, $R_2PX$, $R_3P$, $X_3PO$, $(XO_3)PO$, $(XO)_3P$, $R_3P=O$, $R_3P=S$, $RPO_2$, $PPS_2$, $RP(O)(OX)_2$, $RP(S)(SX)_2$, $R_2P(O)OX$, $R_2P(S)SX$, $RP(OX)_2$, $RP(SX)_2$, $ROP(OX)_2$, $RSP(SX)_2$, $(RS)_2PSP(SR)_2$, and $(RO)_2POP(OR)_2$, where R is an alkyl or aryl, such as a phenyl radical and X is hydrogen, R, or halide. These compounds include primary, $RPH_2$, secondary, $R_2PH$ and tertiary, $R_3P$, phosphines such as butyl phosphine; the tertiary phosphine oxides $R_3PO$, such as tributylphosphine oxide, the tertiary phosphine sulfides, $R_3PS$, the primary, $RP(O)(OX)_2$, and secondary, $R_2P(O)OX$, phosphonic acids such as benzene phosphonic acid; the corresponding sulfur derivatives such as $RP(S)(SX)_2$ and $R_2P(S)SX$, the esters of the phosphonic acids such as diethyl phosphonate, $(RO)_2P(O)H$, dialkyl alkyl phosphonates, $(RO)_2P(O)R$, and alkyl dialkylphosphinates, $(RO)P(O)R_2$; phosphinous acids, $R_2POX$, such as diethylphosphinous acid, primary, $(RO)P(OX)_2$, secondary, $(RO)_2POX$, and tertiary, $(RO)_3P$, phosphites; and esters thereof such as the monopropyl ester, alkyl dialkylphosphinites, $(RO)PR_2$, and dialkyl alkylphosphonite, $(RO)_2PR$ esters. Corresponding sulfur derivatives may also be employed including $(RS)_2P(S)H$, $(RS)_2P(S)R$, $(RS)P(S)R_2$, $R_2PSX$, $(RS)P(SX)_2$, $(RS)_2PSX$, $(RS)_3P$, $(RS)PR_2$ and $(RS)_2PR$. Examples of phosphite esters include trimethylphosphite, triethylphosphite, diisopropylphosphite, butylphosphite; and pyrophosphites such as tetraethylpyrophosphite. The alkyl groups in the mentioned compounds contain one to four carbon atoms.

Other suitable phosphorus-containing compounds include the phosphorus halides such as phosphorus trichloride, bromide, and iodide, alkyl phosphorodichloridites, $(RO)PCl_2$, dialkyl phosphorochloridites, $(RO)_2PX$, dialkylphosphionochloridites, $R_2PCl$, alkyl alkylphosphonochloridates, $(RO)(R)P(O)Cl$, dialkyl phosphinochloridates, $R_2P(O)Cl$ and $RP(O)Cl_2$. Applicable corresponding sulfur derivatives include $(RS)PCl_2$, $(RS)_2PX$, $(RS)(R)P(S)Cl$ and $R_2P(S)Cl$.

Preferred phosphorus-containing compounds include diphenyl phosphine chloride, trimethylphosphite and phosphorus trichloride, phosphoric acid, phenyl phosphine oxychloride, trimethylphosphate, diphenyl phosphinous acid, diphenyl phosphinic acid, diethylchloro thiophosphate, methyl acid phosphate and other alcohol-$P_2O_5$ reaction products.

Incorporation of phosphorus with the zeolite provides a composition having unique properties as a catalytic agent. Thus, the so treated zeolite possesses a greater number of acid sites than the parent zeolite but these sites appear to have a lesser acid strength than those found in the parent zeolite. It is believed that the apparent replacement of the strong acid sites with a greater number of relatively weak acid sites may be responsible for the unique catalytic properties of the phosphorus-containing zeolite.

Reaction of the zeolite with the phosphorus compound is effected by contacting the zeolite with such compound. Where the treating phosphorus compound is a liquid, such compound can be in solution in a solvent at the time contact with the zeolite is effected. Any solvent relatively inert with respect to the treating compound and the zeolite may be employed. Suitable solvents include water and aliphatic, aromatic or alcoholic liquids. Where the phosphorus-containing compound is, for example, trimethylphosphite or liquid phosphorus trichloride, a hydrocarbon solvent such as n-octane may be employed. The phosphorus-containing compound may be used without a solvent, i.e., may be used as a neat liquid. Where the phosphorus-containing compound is in the gaseous phase, such as where gaseous phosphorus trichloride is employed, the treating compound can be used by itself or can be used in admixture with a gaseous diluent relatively inert to the phosphorus-containing compound and the zeolite such as air or nitrogen or with an organic solvent, such as octane or toluene.

Prior to reacting the zeolite with the phosphorus-containing compound, the zeolite may be dried. Drying can be effected in the presence of air. Elevated temperatures may be employed. However, the temperature should not be such that the crystal structure of the zeolite is destroyed.

Heating of the phosphorus-containing catalyst subsequent to preparation and prior to use is also preferred. The heating can be carried out in the presence of oxygen, for example air. Heating can be at a temperature of about 150° C. However, higher temperatures, i.e., up to about 500° C. are preferred. Heating is generally carried out for 3–5 hours but may be extended to 24 hours or longer. While heating temperatures above about 500° C. can be employed, they are not necessary. At temperatures of about 1000° C., the crystal structure of the zeolite tends to deteriorate.

The amount of phosphorus incorporated with the zeolite should be at least about 0.5 percent by weight. With this amount of phosphorus, replacement of a sufficient proportion of the strong acid sites of the zeolite with an increased number of weak acid sites is effected. However, it is preferred in order to increase the replacement of the strong acid sites with an increased number of these weaker acid sites that the amount of phosphorus in the zeolite be at least about 2 percent by weight when the same is combined with a binder, e.g. 35 weight percent of alumina. The amount of phosphorus can be as high as about 25 percent by weight or more depending on the amount and type of binder present. Preferably, the amount of phosphorus added to the zeolite is between about 0.7 and about 15 percent by weight.

The amount of phosphorus incorporated with the zeolite by reaction with elemental phosphorus or phosphorus-containing compound will depend upon several factors. One of these is the reaction time, i.e., the time that the zeolite and the phosphorus-containing source are maintained in contact with each other. With greater reaction times, all other factors being equal, a greater amount of phosphorus is incorporated with the zeolite. Other factors upon which the amount of phosphorus incorporated with the zeolite is dependent include reaction temperature, concentration of the treating compound in the reaction mixture, the degree to which the zeolite has been dried prior to reaction with the phosphorus-containing compound, the conditions of drying of the zeolite after reaction of the zeolite with the treating compound, and the amount and type of binder incorporated with the zeolite.

In practicing the desired alkylation process it may be desirable to incorporate the modified zeolite in another material resistant to the temperatures and other conditions employed in the alkylation process. Such matrix materials include synthetic or naturally occurring substances as well as inorganic materials such as clay, silica and/or metal oxides. The latter may be either naturally occurring or in the form of gelatinous precipitates or gels including mixtures of silica and metal oxides. Naturally occurring clays which can be composited with the modified zeolite include those of the montmorillonite and kaoline familes, which families include the subbentonites and the kaolins commonly known as Dixie, McNamee-Georgia and Florida clays or others in which the main mineral constituent is halloysite, kaolinite, dickite, nacrite or anauxite. Such clays can be used in the raw state as originally mined or initially subjected to calcination, acid treatment or chemical modification.

In addition to the foregoing materials, the modified zeolites employed herein may be composited with a porous matrix material, such as silica-alumina, silica-magnesia, silica-zirconia, silica-thoria, silica-berylia, silica-titania as well as ternary compositions, such as silica-alumina-thoria, silica-alumina-zirconia, silica-alumina-magnesia and silica-magnesia-zirconia. The matrix may be in the form of a cogel. The relative proportions of finely divided modified zeolite and inorganic oxide gel matrix may vary widely with the zeolite content ranging from between about 1 to about 99 percent by weight and more usually in the range of about 5 to about 80 percent by weight of the composite.

Methylation of toluene in the presence of the above-described catalyst is effected by contact of the toluene with a methylating agent, preferably methanol, at a temperature between about 250° C. and about 750° C. and preferably between about 500° C. and about 700° C. At the higher temperatures, the zeolites of high silica/alumina ratio are preferred. For example, ZSM-5 of 300 $SiO_2/Al_2O_3$ ratio and upwards is very stable at high temperatures. The reaction generally takes place at atmospheric pressure, but the pressure may be within the approximate range of 1 atmosphere to 1000 psig. The molar ratio of methylating agent to toluene is generally between about 0.05 and about 5. When methanol is employed as the methylating agent a suitable molar ratio of methanol to toluene has been found to be approximately 0.1–2 moles of methanol per mole of toluene. With the use of other methylating agents, such as methylchloride, methylbromide, dimethylether, methylcarbonate, light olefins or dimethylsulfide, the molar ratio of methylating agent to toluene may vary within the aforenoted range. Reaction is suitably accomplished utilizing a weight hourly space velocity of between about 1 and about 2000 and preferably between about 5 and about 1500. The reaction product consisting predominantly of para-xylene or a mixture of para- and ortho-xylene together with comparatively smaller amounts of meta-xylene may be separated by any suitable means, such as by passing the same through a water condenser and subsequently passing the organic phase through a column in which chromatographic separation of the xylene isomers is accomplished.

The process of this invention may be carried out as a batch-type, semi-continuous or continuous operation utilizing a fixed or moving bed catalyst system. The catalyst after use is conducted to a regeneration zone wherein coke is burned from the catalyst in an oxygen-containing atmosphere, e.g. air, at an elevated temperature, after which the regenerated catalyst is recycled to the conversion zone for further contact with the toluene and methylating agent reactants.

Activation of the above-described phosphorus-modified crystalline aluminosilicate catalyst is accomplished in accordance with the present invention by vapor phase treatment with a mixture of methanol and water at a temperature between about 400° C. and about 650° C. for at least about 1 hour. The preferred temperature of treatment is between about 500° C. and about 650° C. Preferred treating times are generally between about 5 and about 30 hours and particularly between about 10 and about 20 hours, although such time may vary, depending on the amount of phosphorus present. In general, the more phosphorus present, the longer the time required for activation. The mixture of methanol and water employed may vary from a methanol/water volume ratio of 2/1 to 1/2 with an approximately equal volume ratio being particularly preferred. The weight hourly space velocity at which the toluene/water mixture is passed over the described catalyst is within the approximate range of 5 to 50 and preferably between about 10 and about 25. Activation of the phosphorus-modified catalyst, as above described, may be effected after the catalyst has been employed in methylation of toluene or alternatively the catalyst may be activated prior to its use.

The following examples will serve to illustrate the process of this invention without limiting the same:

EXAMPLE 1

A 2 gram sample of HZSM-5 was impregnated with phosphorus by contact with a toluene solution of diphenyl phosphinous acid (2 weight percent concentration), refluxed for 17 hours, after which the solvent was boiled off and the remaining catalyst placed in a furnace in air at 500° C. for 5 hours. The phosphorus content of the catalyst product was 5.08 percent by weight. The catalyst was evaluated by feeding a 2/1 molar solution of toluene/methanol mixture at 550° C. at a weight hourly space velocity of 10 over a 10-hour period. Toluene conversion during this period ranged from 12.2 to 9.9 weight percent and para-xylene content of the xylene product ranged from 81 to 88 weight percent. The catalyst was thereafter activated by treating with a 1:1 volume mixture of methanol/water at 550° C. for 16 hours at a weight hourly space velocity of 10. A 2/1 molar solution of toluene/methanol was again fed over the treated catalyst at 550° C. at a weight hourly space velocity of 10 over a 10-hour period. Toluene conversion during this period ranged from 26 to 20 weight percent and paraxylene content of the xylene product ranged from 75 to 86 weight percent. As a result of the activating treatment with the methanol/water mixture, the average toluene conversion increased from 11 to 23 percent.

EXAMPLE 2

In a manner similar to that of Example 1, 10 grams of HZSM-5 were impregnated with phosphorus by contact with 8 grams of diphenyl phosphine chloride, then refluxed 21 hours, after which the solvent was boiled off. The residue was heated in a furnace at 500° C. for 75 minutes in air to yield a catalyst product containing 6.78 weight percent phosphorus.

Catalyst performance was evaluated by alkylation of toluene with methanol utilizing a 2/1 molar solution of toluene/methanol under the following conditions of time and temperature:

| Run No. | Temp. °C | Time on Stream (Hrs.) | Toluene Conv. % | Percent Paraxylene in Xylene Product | Catalyst Treatment |
|---|---|---|---|---|---|
| 1 | 550 | 1 | 14.4 | 86 | Fresh Catalyst |
| 2, 3 | 600 | 6 | 17.6 – 15.3 | 88 | " |
| 4 | 550 | 1 | 21.7 | 91 | 1:1 volume mixture of MeOH/H$_2$O 550° C, 15.5 hrs. WHSV of 10 |
| 5, 6 | 600 | 4 | 25.6 – 23.3 | 91 | |
| 7 | 550 | 1 | 21.5 | 91 | 1:1 volume mixture of MeOH/H$_2$O 550° C, 16 hrs. WHSV of 10 |
| 8 | 600 | 1 | 24.3 | 91 | |

From the above tabulated data, it will be evident that toluene conversion was increased substantially by the methanol/water treatment between runs 3 and 4.

EXAMPLE 3

Ten (10) grams of HZSM-5 were treated with 4.16 grams of 85% H$_3$PO$_4$ in 150 ml of methanol to yield a catalyst product containing 8.51 weight percent phosphorus after heating in a furnace at 500° C. in air for 4.5 hours.

Catalyst performance was evaluated by alkylation of toluene with methanol utilizing a 1/1 molar solution of toluene/methanol under the following conditions of time and temperature:

| Run No. | Temp. °C | Time on Stream (Hrs.) | Toluene Conv. % | Percent Paraxylene in Xylene Product | Catalyst Treatment |
|---|---|---|---|---|---|
| 1 | 550 | 1 | 12.7 | 77 | Fresh Catalyst |
| 2 | 600 | 1 | 18.0 | 85 | " |
| 3 | 500 | 1 | 24.6 | 95 | 1:1 volume mixture of MeOH/H$_2$O 550° C, 16 hrs. WHSV of 10 |
| 4, 5 | 600 | 4 | 22.6 – 17.4 | 96 | |

It will be seen from the above tabulated data that both the toluene conversion and selectivity to the desired p-xylene product were improved as a result of the methanol/water activation treatment.

EXAMPLE 4

Utilizing the same catalyst as described in Example 1 and employing a toluene/methanol molar feed ratio of 1/1, the following results were observed after treatment of the catalyst with a 1:1 volume mixture of methanol/water at 550° C. for 16 hours at a weight hourly space velocity of 10:

| | Toluene Conversion | | Para-Xylene Selectivity | |
|---|---|---|---|---|
| Temp. °C | Before Treatment | After Treatment | Before Treatment | After Treatment |
| 550 | 20.7 | 37.5 | 82 | 86 |
| 600 | 27.6 | 39.8 | 90 | 90 |

As will be evident from the above data, a significant improvement in toluene conversion was observed as a result of the catalyst activation treatment with methanol/water.

EXAMPLE 5

Ten (1) grams of HZSM-5 1/16 inch extrudate containing 35% Alumina binder was treated with a 5 weight percent trimethyl phosphite solution in toluene, in the vapor phase at a temperature of 115° to 250° C. to yield a catalyst with a phosphorus content of 10 weight percent. The catalyst was calcined for 16 hours at 550° C. in a stream of air flowing through it.

The catalyst was evaluated for alkylation of toluene with methanol by feeding a 4/1 molar toluene/methanol mixture at a weight hourly space velocity of 10. It should be noted that the maximum theoretical toluene conversion is 25 percent, since methanol is the limiting reagent. The following results were obtained at the indicated times and temperatures:

| Run | Temp, °C | Hours | Toluene Conversion Percent | % Para In Xylene Product | Catalyst Treatment |
|---|---|---|---|---|---|
| 1 | 550 | 1 | 13.5 | 51.9 | Fresh Catalyst |
| 2 | 600 | 1 | 11.3 | 73.4 | Fresh Catalyst |

-continued

| Run | Temp, °C | Hours | Toluene Conversion Percent | % Para In Xylene Product | Catalyst Treatment |
|---|---|---|---|---|---|
| 3 | 550 | 1 | 9.2 | 76.1 | Fresh Catalyst |
| 4 | 600 | 1 | 9.1 | 78.1 | Fresh Catalyst |
| 5 | 600 | 1 | 13.2 | 64.8 | Calcined, flowing |
| 6 | " | 1 | 11.2 | 75.5 | air, 600° C |
| 7 | " | 1 | 9.3 | 84.2 | 16 hrs |
| 8 | " | 1 | 8.7 | 84.6 | |
| 9 | " | 1 | 8.5 | 85.9 | |
| 10 | 550 | 1 | 16.1 | 58.2 | Calcined air |
| 11 | " | 1 | 15.5 | 66.6 | 150 cc/min, 550° C |
| 12 | " | 1 | 14.3 | 70.8 | 56 hours |
| 13 | " | 1 | 13.3 | 74.1 | |
| 14 | " | 1 | 12.6 | 76.8 | |
| 15 | 550 | 1 | 19.7 | 58.8 | Treated with MeOH/H$_2$O |
| 16 | " | 1 | 19.3 | 60.2 | 1/1 for 13 hrs at |
| 17 | " | 1 | 19.2 | 61.1 | 550° C followed by a |
| 18 | " | 1 | 19.5 | 62.2 | 5 hr air calcination |
| 19 | " | 1 | 19.4 | 63.2 | at 550° C |

It will be evident from the above tabulated data that toluene conversion increased significantly after the used catalyst was treated with the methanol/water mixture.

EXAMPLE 6

Five (5) grams of HZSM-5 were treated with 6.6 grams of a solution of 20 weight percent H$_3$PO$_4$ in water. The treated composite was dried in an oven at 110° C. and placed in a furnace at 500° C. in air for 56 hours. The catalyst contained 8.17 weight percent phosphorus. In a manner similar to Example 5, it was tested for alkylation of toluene at 600° C. under the following conditions of time and temperature:

| Run | Hrs. Run | Tol. Conv., Mole % | % Para in Xylene Prod. | Catalyst Treatment |
|---|---|---|---|---|
| 1 | 1 | 3.1 | 79.4 | Fresh Catalyst |
| 2 | 1 | 3.0 | 88.5 | |
| 3 | 2 | 4.1 | 92.3 | |
| 4 | 1 | 12.3 | 85.6 | Calcine air 100 cc/min |
| 5 | 1 | 10.8 | 87.1 | 600° C. 1/2 hr; condition |
| 6 | 2 | 13.3 | 90.7 | 1/1 MeOH/H$_2$O 15.5 hrs |
| 7 | 16 | 11.5 | 94.4 | 550° C WHSV = 10; |
| 8 | 1 | 10.3 | 95.9 | then calcine 3 hrs, air, |
| 9 | 1 | 9.9 | 96.0 | 550° C |
| 10 | 1 | 13.7 | 91.0 | Calcine 6 hrs, 600° C, air |
| 11 | 1 | 15.3 | 91.8 | 100 cc/min: condition |
| 12 | 1 | 14.2 | 91.8 | 1/1 MeOH/H$_2$O, 15.5 hrs |
| 13 | 1 | 13.4 | 91.4 | 550° C WHSV = 10 |

It is again evident that the methanol/water activation treatment resulted in a significant increase in toluene conversion.

EXAMPLE 7

In a manner similar to Example 6, HZSM-5 was impregnated with aqueous H$_3$PO$_4$ to yield a catalyst which contained 7.08 weight percent phosphorus after it was removed from an 18 hour treatment in a furnace at 500° C. in air. The catalyst was tested for its ability to alkylate toluene at 600° C. utilizing a 4/1 molar toluene/methanol feed ratio at a weight hourly space velocity of 10. The maximum theoretical toluene conversion was 25 percent since methanol was the limiting reagent. The following results were obtained at the indicated times and temperature:

| Run | Hrs. Run | Tol. Conv., Mole % | % Para in Xylene Prod. | Catalyst Treatment |
|---|---|---|---|---|
| 1 | 1 | 4.7 | 78.8 | Fresh Catalyst |
| 2 | 1 | 4.3 | 85.8 | |
| 3 | 1 | 5.2 | 88.7 | |
| 4 | 1 | 6.6 | 89.0 | Calcined with air at 100 |
| 5 | 1 | 5.8 | 92.4 | cc/min at 550° C for 17 hours |
| 6 | 2 | 6.1 | 93.7 | |
| 7 | 1 | 14.1 | 91.9 | Calcined in air, 600° C, 2.5 |
| 8 | 1 | 13.8 | 92.0 | hrs - Activated 1/1 MeOH/H$_2$O |
| 9 | 2 | 13.5 | 92.1 | 550° C, 15.3 hrs, WHSV = 10 |

It will be evident from the above results that simple calcination in air did not completely activate the catalyst and that substantially improved activation was achieved as a result of treatment with the methanol/water mixture.

EXAMPLE 8

In a manner similar to Example 6, HZSM-5 was impregnated with aqueous H$_3$PO$_4$ to yield a catalyst which contained 8.06 weight percent phosphorus after it was heated for 15.3 hours in air at 500° C.

The catalyst was evaluated for alkylation of toluene at 600° C. utilizing a 4/1 molar toluene/methanol feed mixture at a weight hourly space velocity of 10. The fresh catalyst gave a 2.1 weight percent toluene conversion. After the first 15.5 hour activation with a 1/1 volume mixture of methanol/water, toluene conversion increased to 9.8 weight percent. After the second and third activations, toluene conversion increased to 11.3 and 11.1 percent respectively. All of these activation treatments were carried out at 550° C. for about 15 hours at a weight hourly space velocity of 10. A fourth activation was carried out at 600° C., whereupon toluene conversion increased to 13.8 percent. Selectively to para-xylene was greater than 90 percent in each instance after activation.

EXAMPLE 9

In a manner similar to the previous example, a catalyst of HZSM-5 containing 7.68 weight percent phosphorus had an initial toluene conversion of 0.5 percent. After the first, second and third activations with a 1/1 volume mixture of methanol/water, toluene conversions increased to 9.5 percent, 11 percent and 11.2 percent respectively. A fourth activation was carried out at 400° C. In this instance, the toluene conversion was 11.7 percent, indicating the temperature was too low to increase the toluene conversion significantly.

EXAMPLE 10

In a manner similar to Examples 6-9, a HZSM-5 catalyst with a phosphorus content of 7.46 percent after 61 hours in a furnace in air at 500° C. was obtained. In this case, however, it was activated prior to alkylation use with a 1/1 volume mixture of methanol/water at 550° C. for 15.5 hours at a weight hourly space velocity of 10. The initial toluene conversion was 12.3 percent and the para-xylene selectivity was 90 percent.

EXAMPLE 11

In a manner similar to the previous example, a HZSM-5 catalyst with a phosphorus content of 6.66 percent after 41 hours in a furnace in air at 500° C. was obtained. It was activated immediately and tested in a manner similar to Example 10. The initial toluene conversion was 16.4 percent with an 84 percent selectivity to para-xylene.

It is to be understood that the foregoing description is merely illustrative of preferred embodiments of the invention of which many variations may be made by those skilled in the art within the scope of the following claims without departing from the spirit thereof.

I claim:

1. A process for the methylation of toluene to selectively yield para-xylene which comprises contacting toluene with a methylating agent under methylation conditions in the presence of a catalyst comprising a crystalline aluminosilicate zeolite, said zeolite having a silica to alumina ratio of at least about 12, a constraint index within the approximate range of 1 to 12, said catalyst having been modified by the addition thereto of phosphorus in an amount of at least 0.5 percent by weight and activated by vapor phase treatment with a mixture of methanol and water at a temperature between about 400° C. and about 650° C. for a period of at least about 1 hour.

2. The process of claim 1 wherein said methylating agent is methanol, methyl chloride, methyl bromide, dimethylether or dimethylsulfate.

3. The process of claim 1 wherein said crystalline aluminosilicate zeolite is characterized by a silica/alumina ratio in excess of 30.

4. The process of claim 1 wherein said crystalline aluminosilicate is ZSM-5.

5. The process of claim 1 wherein said methylating agent is methanol.

6. The process of claim 1 wherein said phosphorus is present in an amount of between about 0.5 and about 25 weight percent.

7. The process of claim 1 wherein said mixture of methanol and water comprises a methanol/water volume ratio of 2/1 to 1/2.

8. The process of claim 1 wherein said mixture of methanol and water comprises an approximately equal volume mixture of methanol and water.

9. The process of claim 1 wherein said temperature is between about 500° C. and about 650° C.

10. The process of claim 1 wherein said period is between about 5 and about 30 hours.

11. A method of activating a catalyst comprising a crystalline aluminosilicate zeolite, said zeolite having a silica to alumina ratio of at least about 12, a constraint index within the approximate range of 1 to 12, said catalyst having been modified by the addition thereto of phosphorus in an amount of at least 0.5 percent by weight which comprises subjecting said catalyst to vapor phase treatment with a mixture of methanol and water at a temperature between about 400° C. and about 650° C. for a period of at least about 1 hour.

12. The method of claim 11 wherein said crystalline aluminosilicate zeolite is characterized by a silica/alumina ratio in excess of 30.

13. The method of claim 11 wherein said crystalline aluminosilicate is ZSM-5.

14. The method of claim 11 wherein said phosphorus is present in an amount of between about 0.5 and about 25 weight percent.

15. The method of claim 11 wherein said mixture of methanol and water comprises a methanol/water volume ratio of 2/1 to 1/2.

16. The method of claim 11 wherein said mixture of methanol and water comprises an approximately equal volume mixture of methanol and water.

17. The method of claim 11 wherein said temperature is between about 400° C. and about 650° C.

18. The method of claim 11 wherein said period is between about 5 and about 30 hours.

* * * * *

UNITED STATES PATENT AND TRADEMARK OFFICE
CERTIFICATE OF CORRECTION

PATENT NO. : 4,002,698
DATED : January 11, 1977
INVENTOR(S) : WARREN W. KAEDING

It is certified that error appears in the above-identified patent and that said Letters Patent are hereby corrected as shown below:

Column 5, line 56 Table "0.12-1.0" should read --0.2-1.0--.

Signed and Sealed this

Sixth Day of September 1977

[SEAL]

Attest:

RUTH C. MASON
Attesting Officer

LUTRELLE F. PARKER
Acting Commissioner of Patents and Trademarks